United States Patent [19]
Goldstein

[11] Patent Number: 6,114,135
[45] Date of Patent: *Sep. 5, 2000

[54] MULTIPLE COAGULATION TEST SYSTEM AND METHOD OF USING A MULTIPLE COAGULATION TEST SYSTEM

[76] Inventor: Sheldon Goldstein, 30 S. Adelaide Ave., Penthouse K, Highland Park, N.J. 08904

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/653,770

[22] Filed: May 24, 1996

Related U.S. Application Data

[60] Continuation-in-part of application No. 08/326,323, Oct. 20, 1994, abandoned, which is a division of application No. 07/790,631, Nov. 8, 1991, Pat. No. 5,366,869.

[51] Int. Cl.$^7$ .............................. C12Q 1/56; G01N 21/00
[52] U.S. Cl. ...................... 435/13; 436/16; 424/94.64; 424/530; 424/532; 514/2; 514/802
[58] Field of Search ................................... 435/13, 283.1, 435/286.1, 286.2, 286.3, 286.4, 286.5, 286.7, 287.1, 287.3, 288.2, 288.4, 288.5, 288.6, 288.7, 288.3; 436/69, 79, 16; 422/58, 61, 73; 424/94.64, 530, 532; 514/2, 802

[56] References Cited

U.S. PATENT DOCUMENTS

| | | | |
|---|---|---|---|
| 2,616,796 | 11/1952 | Schilling | 422/73 |
| 3,302,452 | 2/1967 | Leslie | 73/64.43 |
| 3,695,842 | 10/1972 | Mintz | 436/150 |
| 3,836,333 | 9/1974 | Mintz | 422/73 |
| 3,918,908 | 11/1975 | Moyer et al. | 436/69 |
| 4,000,972 | 1/1977 | Braun et al. | 436/69 |
| 4,105,411 | 8/1978 | Biver | 422/73 |
| 4,125,327 | 11/1978 | Margolis | 356/39 |
| 4,135,819 | 1/1979 | Schmid-Schönbein | 356/39 |
| 4,443,408 | 4/1984 | Mintz | 422/73 |
| 4,497,774 | 2/1985 | Scordato | 422/73 |
| 4,534,939 | 8/1985 | Smith et al. | 422/61 |
| 4,599,219 | 7/1986 | Cooper et al. | 422/61 |
| 4,640,896 | 2/1987 | Farrell et al. | 436/34 |
| 4,659,550 | 4/1987 | Schildknecht | 422/73 |
| 4,663,127 | 5/1987 | Jackson et al. | 422/58 |
| 4,671,939 | 6/1987 | Mintz | 422/58 |
| 4,752,449 | 6/1988 | Jackson et al. | 422/73 |
| 4,782,026 | 11/1988 | Baugh et al. | 436/69 |
| 4,865,984 | 9/1989 | Nemerson et al. | 435/287.1 |
| 4,871,677 | 10/1989 | Baugh et al. | 436/69 |
| 4,946,775 | 8/1990 | Yin | 435/13 |
| 5,091,304 | 2/1992 | La Duca et al. | 435/13 |
| 5,110,727 | 5/1992 | Oberhardt | 435/13 |
| 5,184,188 | 2/1993 | Bull et al. | 356/39 |
| 5,300,779 | 4/1994 | Hillman et al. | 250/341.1 |
| 5,302,348 | 4/1994 | Cusack et al. | 422/73 |
| 5,305,745 | 4/1994 | Zacouto | 600/324 |
| 5,325,295 | 6/1994 | Fratantoni et al. | 356/427 |
| 5,350,676 | 9/1994 | Oberhardt et al. | 435/13 |
| 5,366,869 | 11/1994 | Goldstein | 435/13 |
| 5,401,663 | 3/1995 | Yonemura | 436/69 |
| 5,451,509 | 9/1995 | Speck | 435/13 |

FOREIGN PATENT DOCUMENTS

| | | |
|---|---|---|
| 0 434 377 A1 | 6/1991 | European Pat. Off. . |
| WO 89/10788 | 11/1989 | WIPO . |
| WO 91/01383 | 2/1991 | WIPO . |
| WO 91/16453 | 10/1991 | WIPO . |

OTHER PUBLICATIONS

Hemochron® Control Plasma Quality Control Test Kits, International Technidyne Corp., Dec. 1988.

Langdell, Robert D. et al., Effect of Antihemophilic Factor On One–Stage Clotting Tests (1953).

Proctor, Robert R., et al., "The Partial Thromboplastin Time With Kaolin", The Am. J. of Clinical Pathology, vol. 36, No. 3, pp. 212–219, Sep. 1961.

Goldstein, Sheldon, M.D., et al., "Heparin Anticoagulation For Cardiopulmonary Bypass", Futura Pub., 1991.

Austen, D.E., 6, et al., "A Laboratory Manual Of Blood Coagulation", Blackwell Scientific Pub. (1975).

Thrombo Screen® Universal Coagulation Reference Plasma, Pacific Hemostasis (Feb. 1990).

Bick, Rodger L., M.D. "Hemostatis Defects Associated With Cardiac Surgery . . . " Seminars in Thrombosis and Hemostasis, vol. II, No. 3 (1985).

Goodnough, Lawrence T., et al., "On the Need for Improved Transfusion Indicators in Cardiac Surgery", Ann Thorac Surg 1995; 60: 473–480.

(List continued on next page.)

Primary Examiner—Michael G. Wityshyn
Assistant Examiner—Janet M. Kerr
Attorney, Agent, or Firm—Stroock & Stroock & Lavan LLP

[57] ABSTRACT

A multiple coagulation test system and method for determining an appropriate coagulation promoting substance for administration to a patient as a therapy for improving clotting function in said patient has at least three sample wells. One of the wells is for testing a baseline clotting indicator time of a patient's blood to serve as a control sample. Each of the other wells are for testing clotting indicator times of different coagulation promoting substances when mixed with the patient's blood. The coagulation promoting substances are agents or combination of agents capable of improving clotting function in the patient. An appropriate therapy for improving clotting function in the patient is determined by comparison of the baseline control clotting indicator time with the clotting indicator times of the coagulation promoting substances mixed with the patient's blood. Generally, the agent giving the lowest clotting indicator time is selected as an appropriate treatment for reducing hemorrhaging begun. Utilizing the inventive system eliminates the need to use a multiple agent approach, by identifying the most effective course of action in a rapid manner. The system and method are also easily adaptable to test coagulation inhibiting substances.

16 Claims, 2 Drawing Sheets

OTHER PUBLICATIONS

Despotis, G.J. et al., "Prospective evaluation and clinical utility of on–site monitoring of coagulation in patients undergoing cardiac operation", The Journal of Thoracic and Cardiovascular Surgery, 1994 vol. 107, No. 1, pp. 271–279.

Gravlee, Glenn, et al., "Predictive Value of Blood Clotting Tests in Cardiac Surgical Patients", Ann Thorac Surg 1994:58:216–21.

Despotis, G.J. et al., "On–site Prothrombin Time, Activated Partial Thromboplastin Time, and Platelet Count", Anesthology, vol. 80, No. 2, pp. 338–351 (1994).

"Thrombocytopenia in Hypothermia: A Common But Poorly Recognized Complication," British Medical Journal, vol. 291, Jul. 6, 1985, p. 23

Cohen, IJ, "Cold Surgery in Early Infancy"Israeli Med. Sci. vol. 13, No. 4, Apr. 1977, pp. 405–409.

Despotis, G.J. et al., "Factors Associated With Excessive Post–Operative Blood Loss and Hemostatic Transfusion Requirements", Anesth Analg 1996; 82:13–21.

Anesth Analg 1989; 69:142–144, Letters to the Editor.

Johansson B.W. et al., "The Effect of Heparin and Aminocaproic Acid on the Coagulation in Hypothermic Dogs", Acta Physiol. Scand. 1964. 60 267–277.

Spiess, B.D. et al., "Thromboelastography As An Indicator Of Post–Cardio Pulmonary By–Pass Coagulopathies", Journal of Clinical Montoring, vol. 3, No. 1, Jan. 1987, pp. 25–30.

Jian–Sheng Wang "Thromboelastogram Fails to Predict Postoperative Hemorrhage In Cardiac Patients", Ann Thorac Surg 1992; 53: 435–9.

Essell, J.H. et al., "Comparison of Thromboelastography to Bleeding Time and Standard Coagulation Tests in Patients After a Cardio Pulmonary Bypass", Journal of Cardiothoracic and Vascular Anesthesia, vol. 7, No. 4, 1993, pp. 410–415. Dorman, B.H. et al., "Identification of the Patients At Risk for Excessive Blood Loss During Coronary Artery Bypass Surgery", Anesth Analg 1993; 76: 694–700.

Tuman, K.J. et al., "Comprison of Viscoelastic Measures of Coagulation After a Cardiopulmonary By–pass", Anesth Analg 1989; 69: 69–75.

Jobes, D.R. et al., "Increased Accuracy in Precision of Heparin and Protamine Dosing" The Journal of Thracic and Cardiovascular Surgery vol. 110, No. 1, pp. 36–45 (Jul. 1995).

Despotis, G.J. et al., "The Impact of Heparin Concentration and Activated Clotting Time Monitoring on Blood Conservation", J. Thorac Cardiovascular Surg. 1995; 110: 46–54.

Burns, E.R. "Physiologic Response To Traumatic Bleeding", pp. 3–18, Blackwell Scientific, Boston, USA, 1987, in Clinical Management Of Bleeding And Thrombosis, Chapter 1.

Hathaway, William E. et al, "Disorders of Hemsotasis and Thrombosis", McGraw–Hill, Inc., pp. 338–241, 448–449 (1993).

Smiley, R.K. et al., "Studies On The Pronged Bleeding Time In Von Willebrand's Disease", Thrombosis Research, vol. 53, No. 5, pp. 417–426 (1989).

Chediak, Juan R., et al "Platelet Function and Immunologic Parameters in von Willebrand's Disease Following Cryoprecipitate and Factor VIII Concentrate Infusion", The American Journal of Medicine, vol. 62, Mar. 1977, pp. 369–375.

Hoffman, M. et al., "Fibrinogen content of low–volume cryoprecipitate", Transfusion, vol. 27, No. 4–1987, pp. 356–358.

Hattersley, Paul G., "The Treatment of Classical Hemphilia With Cryoprecipitates", JAMA, vol. 198, No. 3, Oct. 17, 1966, pp 153–57.

Janson, Paul A., et al. "Treatment Of The Bleeding Tendency In Uremia With Cryoprecipitate", The New England Journal Of Medicine, vol. 303, No. 23, Dec. 4, 1980, pp 1318–22.

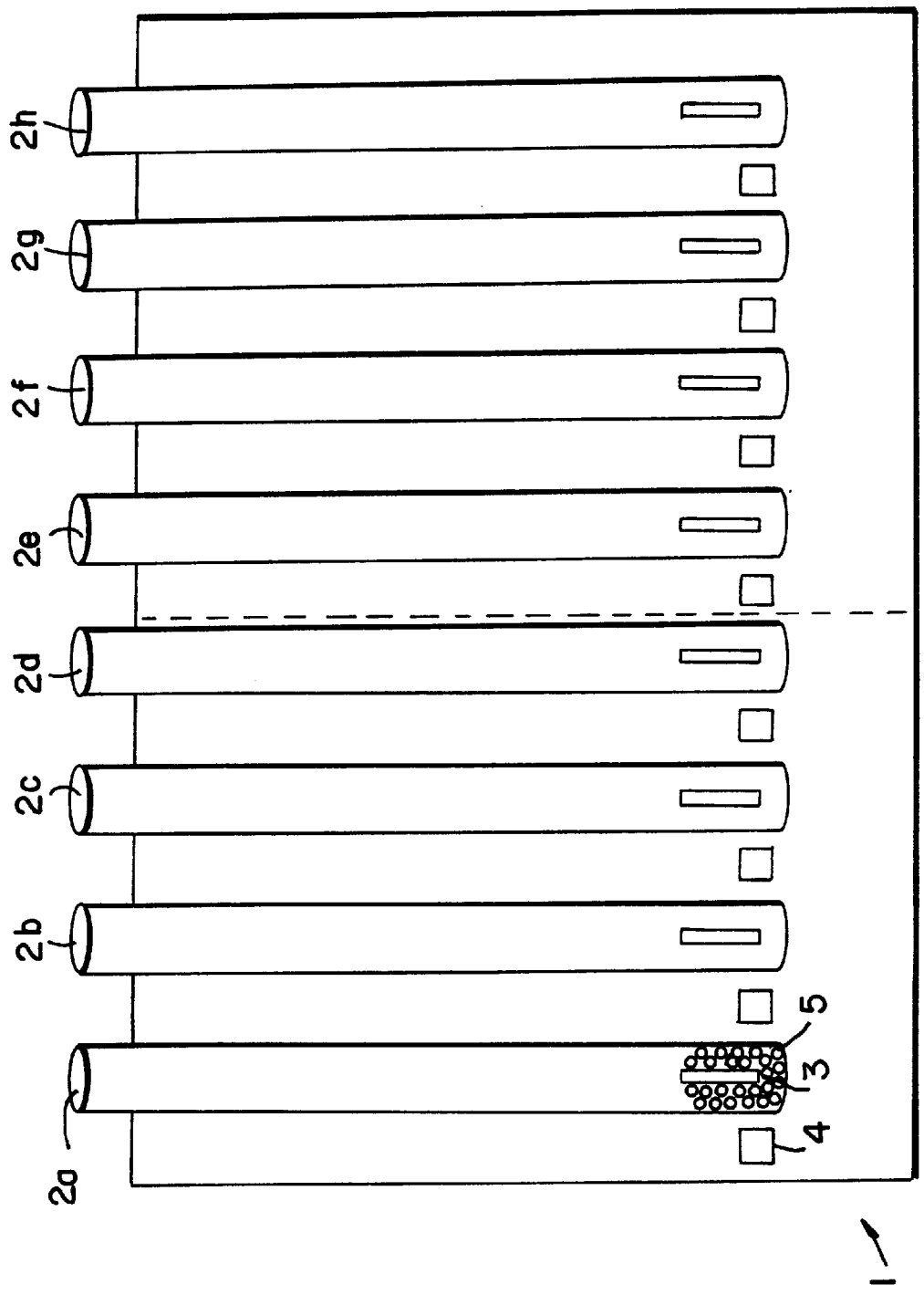

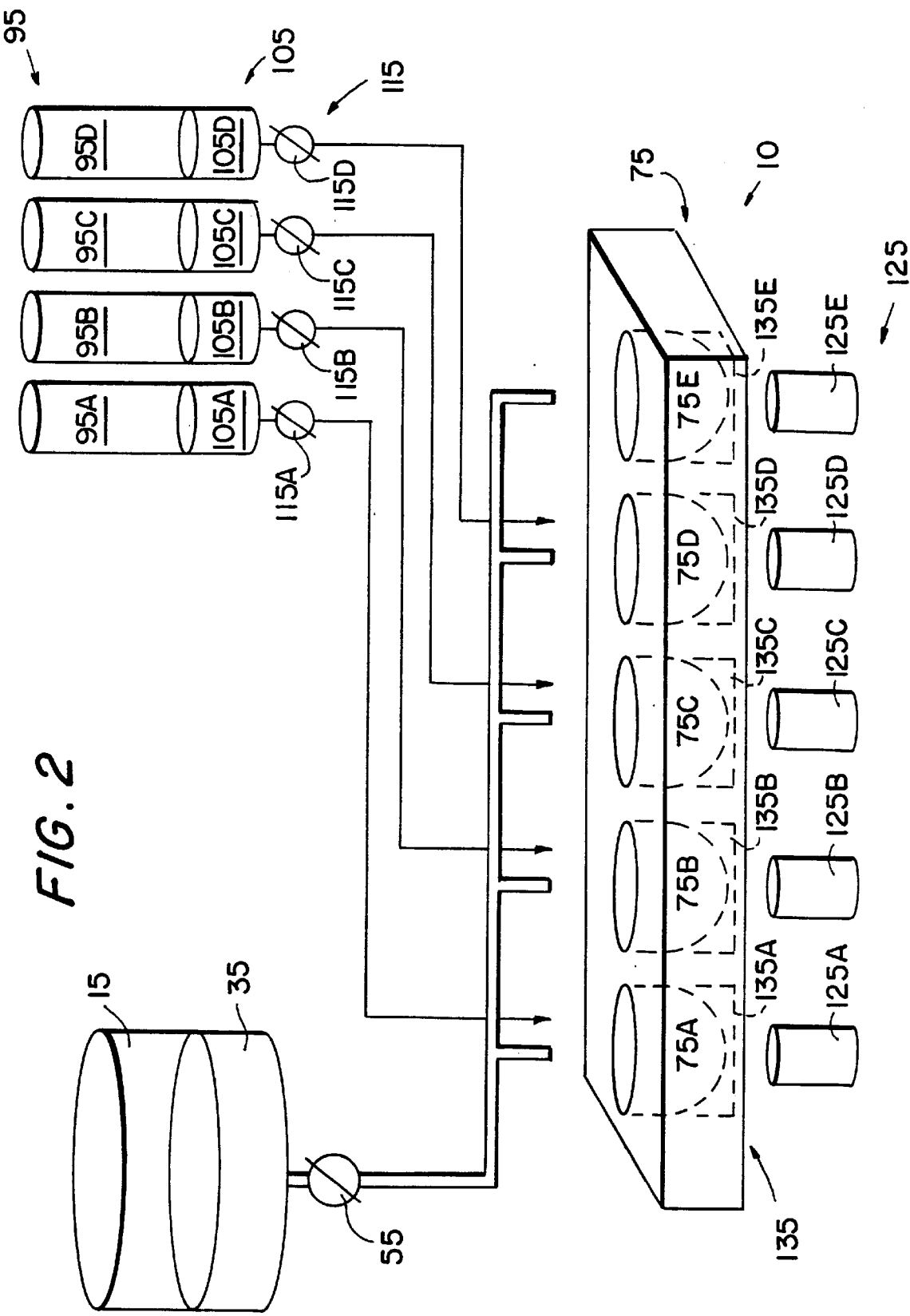

MULTIPLE COAGULATION TEST SYSTEM AND METHOD OF USING A MULTIPLE COAGULATION TEST SYSTEM

CROSS REFERENCE TO RELATED APPLICATIONS

This is a continuation-in-part of application Ser. No. 08/326,323, filed on Oct. 20, 1994 (now abandoned), which is a divisional of application Ser. No. 07/790,631, filed Nov. 8, 1991, and now patented as U.S. Pat. No. 5,366,869, granted Nov. 22, 1994. The contents of each of these applications are incorporated herein by reference.

BACKGROUND OF THE INVENTION

This invention relates generally to a method and system for use in quickly determining the causes and selecting an appropriate therapeutic treatment for peri-operative or non-surgical hemorrhaging in a patient having a compromised coagulation function or other coagulopathy. The present invention also relates to the field of medical diagnosis and treatment of patients with compromised coagulation function or other coagulopathy generally, and more particularly to the analysis of a patient's blood coagulation function and the influence coagulation promoting substances and/or coagulation inhibiting substances may have on that patient's blood coagulation function. The invention even more particularly relates to an apparatus and system for particularly selecting appropriate coagulation promoting substances for administration to a patient with compromised blood coagulation function as a therapeutic treatment for that patient or, alternatively for particularly selecting appropriate coagulation inhibiting substances for administration to a patient as an agent for inducing inhibition of clotting for that patient.

It is well known in the art to inhibit the coagulation of a patient's blood by administering various anticoagulant substances, such as, for example, heparin, to the blood, which compromises the patient's blood coagulation function (i.e., causes iatrogenic coagulopathy). Inhibiting the coagulation of blood in a patient is particularly useful during medical procedures which may, for example, utilize extracorporeal circulation, such as medical procedures including cardiovascular surgery and hemodialysis. After the medical procedure requiring compromised coagulation function is completed, it is then often desirable to restore coagulation function in the blood of the patient. Again, it is well known in the art to restore coagulation function in the blood of a patient having compromised coagulation function by administering known agents, such as, for example, protamine, that counteract the anticoagulant substance. An illustrative example of the appropriateness of the therapeutic use of an anticoagulation substance, followed by restoring proper coagulation function with an agent that counteracts the anticoagulation substance, follows.

A heart-lung machine is typically used during heart surgery for coronary artery bypass, valvular replacement or proximal aortic reconstruction. The heart-lung machine substitutes for the function of a patient's heart muscle to pump blood throughout the patient's body, and substitutes for lung function by removing carbon dioxide and adding oxygen to the patient's blood.

To use the heart-lung machine, inhibition of the coagulation cascade in the patient's blood is required in order to prevent clot formation on the interior surfaces of the heart-lung machine. In the coagulation cascade generally, fibrin formation is initiated by Factor XII, Prekallikrein and high molecular weight kininogen, or by Factor XI in the intrinsic coagulation pathway, or by release of "tissue factor" in the extrinsic coagulation pathway. The coagulation cascade ultimately results in the conversion of fibrinogen to fibrin.

The arrest or inhibition of the coagulation cascade in a patient's blood is typically accomplished by administering a coagulation inhibiting substance such as heparin to the patient. Heparin impedes coagulation by enhancing the effectiveness of anti-thrombin III, a naturally occurring substance in the blood which inhibits coagulation. Heparin inhibits proper coagulation function by causing a conformational change in anti-thrombin III that exposes additional factor binding sites on the anti-thrombin III molecule, which increases the ability of anti-thrombin III to bind with factors XIIa, XIa, IXa and Xa, which in turn reduces their ability to participate in the proper formation of fibrin. After the period of cardiopulmonary bypass is completed, the heparin effect is reversed by administering a heparin-antagonist agent, such as protamine.

Determining the proper number of units of heparin to be administered to a patient just prior to a medical procedure requiring compromised coagulation function is generally complicated because of two independent phenomena. First, the amount of heparin that must be injected into a patient to achieve a certain plasma heparin concentration varies from patient to patient due to an inherent difference in heparin potency and/or affinity of antithrombin III for heparin. Second, a given heparin level in a patient's plasma does not necessarily reflect an exact state of anticoagulation in that particular patient because of a number of factors peculiar to certain individual patients, such as extravascular depots, hemodilution, hypothermia, heparin resistance and anti-thrombin III deficiency.

Thus, it has been desirable to measure the coagulation function of a patient just prior to performance of the medical procedure. To determine whether the amount of heparin administered has effectively reduced the ability of the patient's blood to clot, typically the Activated Coagulation Time (ACT) is measured. The ACT was introduced by Hattersley in 1966 and is a method for the rapid determination of the Lee-White whole blood clotting time. Although initially performed by manual rotation of a test tube containing a patient's blood and a visual inspection for the presence of a clot, the ACT test is currently typically performed via an automated method performed by a machine known as the HEMOCHRON (International Technidyne, Edison, N.J.) or, the HEMOTEC device (Medtronic Blood Management, Parker, Colo.). Other devices and laboratory tests are also used to measure coagulation function.

As an example, with the HEMOCHRON device, typically a sample containing two (2) cc's of whole blood is withdrawn from the patient and placed in an ACT tube and the start time recorded. The tube is shaken to mix the blood with a diatomaceous powder which activates coagulation by its high surface area. The tube is also simultaneously warmed to normal body temperature, or 37° C. A magnetic rod placed in the tube is observed by a magnetic detector, and when coagulation occurs, the rod is displaced, signaling completion of the test. This coagulation time, which is the elapsed time from the start of the test until coagulation is detected, is then recorded, and the difference between the coagulation time and the start time is known as the ACT time. A normal ACT has been described as taking from 100 to 140 seconds in a patient with normal coagulation function. However, significant inter-device and institutional factors may affect the results. Thus, it is common practice to establish a control, or normal ACT reading by testing the patient's blood before a medical procedure and before administration of a coagulation inhibiting substance.

The ACT is currently first measured prior to the medical procedure to provide this baseline control ACT or "normal ACT" and then is measured again after administration of heparin, or other coagulation inhibiting substance to document whether a safe level of anticoagulation has been attained. The ACT is also measured serially during the procedure or heart surgery, usually about every 30 minutes, to be sure that adequate anticoagulation is maintained since the heparin may normally be metabolized and/or excreted by the patient.

The ACT is also used after the procedure or heart surgery is completed. At this time, the heart has been restarted and is pumping blood through the lungs where oxygen is added to the blood and carbon dioxide is removed. Use of the heart-lung machine is completed and thus it becomes desirable to restore proper coagulation function to the patient.

The heparin anticoagulation effect is generally reversed by the administration of an antagonist to heparin, such as, for example, protamine. Protamine is polycationic and forms a complex with heparin, thus reversing heparin's effects on anti-thrombin III. After administering protamine, the ACT is measured to determine if the protamine has adequately reversed the effects of heparin. Thus, the ACT is run and the ACT time compared to the normal or baseline ACT time, which was measured prior to the operation.

Sometimes, however, the administration of protamine does not fully return the ACT to the normal or baseline condition. When this occurs, it is often the case that, in addition to an elevated ACT, the patient may also be experiencing uncontrolled bleeding as a result of the operation. Although many clinicians associate an increased ACT, and therefore, the cause of the patient's bleeding, with a prolonged heparin effect, the ACT is limited in that it is a test of essentially the entire coagulation cascade or system, and as such, it is affected by other changes in the coagulation cascade which may actually be responsible for the continued coagulopathy or compromised coagulation function indicated, in this case, both by the elevated ACT and by the uncontrolled bleeding of the patient. Therefore, an elevated ACT after heparin reversal with protamine does not necessarily indicate that residual (i.e., unneutralized) heparin is the cause of the elevated ACT. An elevated ACT can indicate a compromised coagulation function due to factors other than, or in addition to residual heparin. For example, hypothermia, decreased levels of fibronectin, destruction of, or abnormal function of serine protease (proteins required for blood to clot, otherwise known as clotting factors), hypofibrinogenemia, fibrinolysis and platelet abnormalities, both qualitative and quantitative, can influence the ACT and also be responsible for the compromised coagulation function responsible for the patient's bleeding.

Because of the many factors involved in the coagulation cascade and possible reasons for a patient's compromised coagulation function, there is a recognized need for tests which permit an analytical approach to diagnosis and treatment of compromised coagulation function. Typically, blood analysis laboratories test coagulation function in a patient's blood by using tests such as prothrombin time (PT), activated partial thromboplastin time (PPT) and platelet count (PLT). Unfortunately, the clinical utility of these tests is limited by the delay in obtaining results. There have been recent developments in instrumentation for on-sight testing which allows rapid return of results of coagulation function tests. Despotis, Santoro, et al. *On Sight Prothrombin Time,* *Activated Partial Thromboplastin Time And Platelet Count,* Anesthesiology 80:338–351, 1994, discuss using a panel of rapidly performed screening tests to delineate the etiology of compromised coagulation function in patients and conclude that the use of on sight coagulation tests can reduce blood product administration by more precisely determining what therapy to use. Unfortunately, even this protocol requires a number of different tests, each requiring expensive instrumentation, and each merely determining the general area of coagulation function that is abnormal, rather than determining an appropriate therapy. Furthermore, Gravlee, Arora, et al. *Predictive Value Of Blood Count Clotting Test In Cardiac Surgical Patients,* Ann Thorac. Surg., 58: 216–221, 1994 studied the same tests and concluded that "the predictive values of the tests are so low, it does not appear sensible to screen patients routinely using these clotting tests shortly after cardiopulmonary bypass."

As discusseed above, since an increased ACT is often associated with a prolonged heparin effect, clinicians may be inclined to administer an additional protamine dose when confronted with a bleeding patient and coupled with an elevated ACT. However, an elevated ACT, as discussed above, may not be due to residual heparin at all. In fact, an elevated, or increased ACT time after extracorporeal circulation may be due to any of the following etiologies: for instance, qualitative or quantitative abnormalities of platelets, factors I, II, V, VII, VIII, IX, X, XI, XII, Prekallikrein, high molecular weight kininogen, tissue factor, factor XIII, calcium ion deficiencies, and other etiologies such as fibrinolysis and disseminated intra-vascular coagulation (DIC) can all be implicated in abnormal coagulation. Each of these etiologies or factors may be implicated in one or more of the various stages of clot formation. Therefore, adding an additional dose of protamine may not successfully restore proper coagulation function in the patient. In fact, it is now increasingly more common to measure the patient's heparin level at the conclusion of the extracorporeal circulation procedure for determining the appropriate amount of protamine to use in the first instance for completely counteracting the remaining heparin.

One device currently used to assist in determining the appropriate protamine dose in order to completely counteract the heparin effect is the HEPCON (HemoTech Inc., Englewood, Colo.). The HEPCON device consists of four chambers which contain specific, generally increasing, amounts of protamine, thromboplastin and diluent. Air bubbles percolate through the blood sample in each chamber until a photocell detects clot formation in one of the chambers. Based upon the patient's height and weight, the device computes the proper amount of protamine needed to counteract the amount of heparin remaining in the patient's blood at the conclusion of the procedure. In essence, this device confirms whether or not a patient's bleeding tendency is due to excess heparin. If protamine administration is followed by obtaining an elevated ACT and a HEPCON test produces no shortening in clotting time between the baseline control sample and the samples with additional protamine added, this indicates that heparin is not circulating and it is likely that one or more other etiologies may be responsible for the compromised coagulation function and hemorrhaging.

As discussed above, bleeding in general, surgical or non-surgical patients, including those involved in cardiopulmonary bypass surgery where there is no longer any circulating heparin, may be due to a compromised coagulation function due to a decreased level or abnormal function of coagulation factors such as factors II, V, VII, VIII, IX, X, XI, XII, XIII, Prekallikrein, high molecular weight kininogen or tissue factor, and fibrinogen, as well as thrombocytopenia, abnormal platelet function, decreased levels of fibronectin, complement activation, fibrinolysis, disseminated intra-vascular coagulation or calcium ion deficiency. Decreased levels of serine proteases and platelets could be due to low grade coagulation which occurred during the extracorporeal circulation with attendant consumption of the factors and platelets used in forming clots, or damage and destruction sustained to blood cells when exposed to the surface of the heart-lung machine, and/or the oxygenator.

The anesthesiologist and surgeon are thus often faced with the situation that a patient is bleeding significantly and it is not due to excess heparin in the blood. A similar situation may occur in a patient with massive bleeding due to a medical etiology. Because of the numerous possibilities of which particular coagulation factor or combination of coagulation factors or other agents, such as, for example, platelets, calcium ion or pharmacologic agents are needed to restore the coagulation cascade and coagulation function and stem the hemorrhaging, combined with the extremely limited amount of time available, the patient is frequently treated with a "shotgun therapy," for example, by administration of many different coagulation promoting substances or other therapies at once, including, typically, the administration of platelets, fresh frozen plasma (FFP), and cryoprecipitate, and sometimes pharmacologic agents as well, such as desmopressin acetate (DDAVP) and sometimes epsilo-amino caproic acid (AMICAR). For example, Despotis, Santoro, et al. *Prospective Evaluation And Clinical Utility Of On sight Monitoring Of Coagulation In Patients Undergoing Cardiac Operation*, J. Thorac. Cardiovasc. Surg. 107:271–9, 1994, recognized that "because of the frequent absence of available laboratory data, standard treatment of microvascular bleeding after CPB is often non-specific (e.g., additional protamine, fresh frozen plasma, and platelet concentrates). In addition, hemostatic blood products are frequently administered on a prophylactic basis in an attempt to distinguish microvascular bleeding from surgical bleeding. Neither approach constitutes an optimal strategy for patient treatment."

Since the use of platelets, fresh frozen plasma and cryoprecipitate all carry the increased risk of disease transmission, a system to rapidly determine if one or two specific coagulation promoting therapies would be sufficient to restore coagulation function, would decrease the risk to the patient of contracting hepatitis, aids, and numerous other blood-borne diseases. Furthermore, in cases where it is determined that DDAVP or AMICAR, recombinant factors, or other pharmacologic agents would, by themselves be therapeutic, and would restore proper coagulation function, the patient would be spared transfusion of blood products altogether.

An additional reason to rapidly determine the specific appropriate therapy for restoring proper coagulation function is that as long as there is a compromised coagulation function or other deficiency in blood coagulation (i.e., a coagulopathy), the patient will require transfusion of more and more packed red blood cells (PRBCs). In addition to the increased risk of disease transmission, transfusion of large amounts of PRBCs dilutes the patient's existing coagulation factors and platelets in their blood, resulting in a condition know as "dilutional coagulopathy," thus possibly further compromising the coagulation function and contributing to the degree of hemorrhaging.

At present, complete, definitive coagulation function studies can only be done in the laboratory, which takes too long to be of use in determining a specific coagulation promoting substance to be used as a therapy against massive hemorrhage, whether under operating room or non-operating room conditions. There is thus a need for a method that is rapid enough to allow a doctor to determine and administer a specific coagulation promoting substance as a therapy for restoring proper coagulation function under the severe time constraints posed by an episode of rapid massive bleeding whether in the operating room or otherwise.

In addition, as discussed above in relation to disseminated intra-vascular coagulation or microvascular bleeding, certain post-operative coagulopathy is associated with depleted amounts or reduced functioning of platelets or coagulation factors. Since more complete inhibition of coagulation before instituting cardio-pulmonary bypass, or beginning any surgery associated with fibrinolysis (which includes non-bypass surgery, such as lengthy hip replacement surgery, and others), will provide an additional level of protection from destruction or reduction in amount or functioning of platelets or factors during cardio-pulmonary bypass or surgery associated with fibrinolysis, it is useful to be able to predict the most appropriate level of inhibition of coagulation which would best preserve platelets or factors so that they are available in the appropriate amounts and are functional to effect coagulation when cardiopulmonary bypass or surgery associated with fibrinolysis is completed.

SUMMARY OF THE INVENTION

Accordingly, it is the object of the present invention to provide an improved system and method for reliably determining which specific coagulation promoting substance, selected from a number of coagulation promoting substances, will best restore proper coagulation function in a patient's blood. It is a further object to provide a system and method which is automated and which can be used any number of times, as necessary, during extended medical procedures.

It is yet another object of the present invention to provide a system and a method in which various coagulation promoting substances are added to a patient's blood in a manner which closely simulates the actual state in which the patient's blood is circulating, and testing various coagulation promoting substances in that blood in order to determine which coagulation promoting substances most appropriately restore proper coagulation function in that patient.

It is a further object of the present invention to provide a system and method which provides specific indications of the particular coagulation promoting substances which will positively influence the coagulation function of blood in a patient who has a compromised coagulation function or coagulopathy and may be bleeding.

It is also an object of the present invention to provide a system and method which provides specific indications of the particular coagulation inhibiting substances which will negatively influence coagulation function of blood for minimizing intra-vascular coagulation and preserving the quantity and functioning of platelets or coagulation factors during medical procedures which may cause fibrinolysis.

It is a still further object to provide a system which can be used rapidly, yet is sufficiently specific to identify particular coagulation promoting factors or substances which can be used to treat intra-operative, post-operative or non-surgical bleeding.

Accordingly, one embodiment of a testing method and system for determining an appropriate coagulation promoting substance for administration to a patient as a therapy for improving clotting function in said patient of the present invention includes a group of at least three sample wells for receiving a selected amount of a patient's blood. One of the sample wells is substantially free of coagulation promoting substance and is used for testing a baseline clotting indicator time of the patient's blood to serve as a control sample. The other sample wells contain different coagulation promoting substances for testing clotting indicator times of the patient's blood when mixed with these different coagulation promoting substances. The coagulation promoting substances are an agent or combination of agents capable of improving clotting function in the patient. The sample wells are constructed and arranged to allow for detection of a clotting indicator in the patient's blood for determining clotting indicator time and an appropriate therapy for improving clotting function in the patient is determined by comparison of the baseline clotting indicator time of the control sample with the clotting indicator times of the patient's blood mixed with the coagulation promoting substances.

Another embodiment of the present invention provides a method and system which includes a plurality of wells, each of which contains a comparable amount of a patient's blood and an equivalent dose of a particular coagulation promoting substance, these coagulation promoting substances or therapies, being generally, one or a combination of coagulation promoting agents, individually. For example, one well may have an anti-heparin agent such as protamine, or may have fresh frozen plasma or platelets or AMICAR contained therein. The standard ACT test, or any other clotting indicator detection system will then be carried out on the patient's blood in combination with the coagulation promoting substance, i.e. each well will provide clotting indicator detection such as by including, for example, a magnetic rod coupled with an associated detector, and the wells may be agitated and have their temperature elevated to approximate normal body temperature. Thus, the effects on coagulation function will be assessed by noting formation of a clot or other clotting indicator, such as changes in the quality of the blood which indicate improved clotting function, as for example, may be observed with a photo-cell detector or changes in viscosity or other parameters indicative of clot formation. Depending on the most effective treatment for increasing coagulation function, a suitable treatment will be determined and administered to the patient.

Typically, the clot detection or other clotting indicator, such as the ACT test, takes approximately two to five minutes and can be done in an operating room without utilizing a separate laboratory facility. Of course, a photo-cell detector or other detecting means may also be used so long as the endpoint of the test of the inventive system is the detection of a clot or other clotting indicator within the patient's blood, generally in a timed manner.

According to a method and system of determining an appropriate coagulation promoting substance for administration to a patient as a therapy for improving clotting function in said patient of the invention, provided are the steps of adding a selected amount of a patient's blood to each of at least three sample wells. One of the sample wells is for testing a baseline clotting indicator time of a patient's blood to serve as a control sample and the other sample wells are for testing clotting indicator times of the patient's blood when mixed with different coagulation promoting substances. The coagulation promoting substances are an agent or combination of agents capable of improving clotting function in the patient. A selected equivalent dose amount of the coagulation promoting substances is added to the other sample wells and the elapsed time till a blood clotting indicator in the sample wells is detected whereby an appropriate therapy for improving clotting function in said patient is determined by comparison of the baseline clotting indicator time of the control sample with the clotting indicator times of the patient's blood mixed with the coagulation promoting substances.

According to an automated testing method and system for determining an appropriate coagulation promoting substance for administration to a patient as a therapy for improving clotting function in the patient of the invention, there includes a holder for containing a patient's blood. An aliquot meter is in fluid communication with the holder for withdrawing a predetermined measured amounts of the patient's blood. Various reservoirs each contain different coagulation promoting substances. The coagulation promoting substances are an agent or combination of agents capable of improving clotting function in said patient. Dosing meters are in fluid communication with the reservoirs for withdrawing a preselected equivalent dose amounts of the coagulation promoting substances from the reservoirs. At least three sample wells, one of which sample wells receives a measured amount of the patient's blood for testing a baseline clotting indicator time of said patient's blood to serve as a control sample and the other wells receive measured amounts of the patient's blood and the equivalent dose amounts of the coagulation promoting substances for testing clotting indicator times of the patient's blood when mixed with the different coagulation promoting substances. The aliquot meter delivers the measured amount of the patient's blood to each of the wells; and the dosing meters deliver each of the coagulation promoting substances from each of the reservoirs individually to a corresponding one of the other wells. An appropriate therapy for improving clotting function in the patient is determined by comparison of the baseline clotting indicator time of the control sample with the clotting indicator times of the patient's blood mixed with the coagulation promoting substances.

According to a testing system and method for determining an appropriate coagulation inhibiting substance for administration to a patient as a therapy for inhibiting clotting function in the patient is provided which includes at least three sample wells for receiving a selected amount of a patient's blood. At least one of the sample wells is for measuring a baseline clotting indicator time of the patient's blood as a control sample. The control sample wells are substantially free of coagulation inhibiting substance. At least two other sample wells for are for measuring a test clotting indicator time of the patient's blood and coagulation inhibiting substance as a test sample. These test sample wells each contain a different coagulation inhibiting substance. The coagulation inhibiting substance are an agent or combination of agents capable of inhibiting clotting function in said patient. The sample wells are constructed and arranged to allow detection of a clotting indicator in the patient's blood for measuring clotting indicator times so that an appropriate therapy for inhibiting clotting function in the patient is determined by comparison of the baseline clotting indicator time of the control sample with the test clotting indicator time of the patient's blood and the coagulation inhibiting substance.

In the simplest case, when the system and method is used to determine an appropriate coagulation promoting substance to use therapeutically for restoring normal coagulation function in the patient's blood will generally be the well in which coagulation or clotting occurs first. However, due to the intricacies of the coagulation cascade and other aspects of clot formation and particularly the artificial nature of in vitro testing, the possibility exists that an appropriate coagulation promoting substance is selected by the device which is not the coagulation promoting substance added to the well in which coagulation or clotting or other clotting indicator is detected, occurs first. If the well containing platelets and an aliquot of the patient's blood exhibits clotting or coagulation at a time shorter than the time expected when added to the patient's blood, this may indicate that platelets are an appropriate therapy, or for example, this may indicate the patient's platelets, though present in adequate numbers, are inadequately functioning, and/or are present in inadequate number. It is also possible that, as an example, it may be that, in general, in vitro coagulation is enhanced by the addition of platelets even if sufficient platelet amount and functioning is present in the patient's blood. Therefore, even if the patient's blood has the appropriate amount of platelets, and platelet functioning is normal, adding additional platelets to that patient's blood may still decrease coagulation time relative to the standard baseline blood clotting time determination. However, additional platelets may not be the most appropriate therapy. For example, it is possible that blood clotting function will be improved, and cause a shorter ACT time by the small amount of plasma in which the platelets are suspended.

Because it is not uncommon for patients to become hypothermic during extended extracorporeal circulation procedures, and it is well-known that hypothermia can play a significant role in retarding coagulation, it may often be necessary to maintain the samples in the wells at the current temperature of the patient rather than at normal body temperature, or at some other temperature. Then, addition wells may contain samples at normal blood temperature as well. Thus, it may well be found from observing the clotting time in the normal body temperature wells relative to the decreased temperature wells, that proper blood coagulation function can be restored simply by restoring the patient to normal body temperature. In this case, since a patient may continue bleeding while and until their temperature is restored to normal, by observing the wells containing a patient's blood and coagulation promoting substance, an appropriate therapy can also be administered. In addition, this may indicate that warming the patient will treat the coagulopathy.

The preferred embodiment of the system and method of the invention provides for a removable and replaceable holder for containing a patient's blood and removable reservoirs for containing the coagulation promoting substances. A replaceable holder is used so that fresh samples of the patient's blood can be tested simply by removing the old holder, and replacing it with a new holder containing the patient's recently withdrawn blood. The individual reservoirs for containing coagulation promoting substances are removable to allow convenient filling and preparing them with coagulation promoting substances which will typically be freshly filled by a blood bank technician or by the physician or clinician with enough coagulating promoting substances taken from the snippets at the corner of the various coagulation promoting substance bags to provide for many individual tests. Thus, the system and method tests the patient's blood with the actual coagulation promoting substances from blood products which will be used for that patient.

Alternatively, prepared frozen coagulation promoting substances, as for example, plasma or cryoprecipitate may be obtained from known normal AB blood donors or bovine blood may be used in the reservoirs as the coagulation promoting substances. This will be the case where blood products are not provided in advance of a procedure for a particular patient and held ready for them, in which case those blood products can be used in the reservoirs, as discussed above. It may also be advantageous, to include synthetic or pharmacological agents which indicate particular coagulation factor deficiencies in quantity or function, or other etiologies.

In addition, the system and method of the invention may be easily adapted for determining a most appropriate dose of the coagulation promoting substance chosen as a therapy for a patient with compromised coagulation function. Metered aliquots of the patient's blood are added to each of the wells. Increasingly additive amounts of the single coagulation promoting substance or combination of substances from the reservoir containing the coagulation promoting substance to be administered as a therapy are metered from that reservoir by the dosing meter into each well. The appropriate dose is determined by the lowest equivalent dose in a well which provides sufficient blood clotting to indicate proper coagulation function.

Also, the system and method of the invention may be easily adapted for determining an appropriate coagulation inhibiting substance for administering to a patient for more completely inhibiting coagulation function to prevent intravascular clotting. In this case, coagulation inhibiting substances are used rather than the coagulation promoting substances in the previous embodiments.

Utilizing the present invention, a device is provided for immediate operating room or non-operating room use which produces results indicating a proper course of treatment without resort to a shotgun approach which requires an addition of multiple agents to a patient and thus avoids several of the complications inherent in utilizing such an approach. The device thus allows rapid determination of a specific treatment in a hemorrhaging situation without awaiting standard laboratory test results.

Still other objects and advantages of the invention will in part be obvious and will in part be apparent from the specification.

The invention accordingly comprises the several steps and the relation of one or more of such steps with respect to each of the others, and the apparatus embodying features of construction, combinations of elements and arrangement of parts which are adapted to effect such steps, all of as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings in which, FIG. 1 schematically shows one embodiment of the multiple coagulation test system of the present invention for performing a multiple coagulation time test for determining an appropriate coagulation promoting substance for administration to a patient.

FIG. 2 schematically shows an embodiment of an automated multiple coagulation test system of the present invention for performing a multiple coagulation time test for determining an appropriate coagulation promoting substance for administration to a patient.

DETAILED DESCRIPTION OF THE INVENTION

A first embodiment of the multiple coagulation test system for determining an appropriate coagulation promoting substance for administration to a patient as a therapy for improving clotting function in said patient is described.

Referring to FIG. 1, a system 1 according to the invention is shown schematically. The system 1 has, for example, 8 tubes 2A-H, each tube capable of allowing coagulation or clotting indicator in a blood sample contained therein to be detected, for example, by photo-optic detection by a photo-optic detector (not shown) or, by a magnetic detector, in which case, tubes 2A-H may each contain a magnetic rod 3, and each tube 2A-H has a magnetic detector 4 associated with it. Each tube 2A-H may additionally contain a quantity of diatomaceous powder 5 for increasing the surface area, or other substance to activate coagulation, and an individual or combination of coagulation promoting substances capable of restoring proper coagulation function in a patient's blood, for promoting coagulation function.

The tubes may be preferably sized to accept, for example, a 2.5 cc sample of a patient's whole blood. To each tube 2A-H is added a different coagulation promoting substance which is a potential therapy for restoring coagulation function, based upon a standard dose for a 70 kg adult with a blood volume of 5,000 cc. The dose is then divided by 2000 (to be equivalent to the blood sample size of 2.5 cc) to obtain an equivalent dose to be added to each tube 2-A H, which is appropriate for the 2.5 cc of patient's blood contained therein.

Tube 2A may be a standard baseline control and will typically contain the patient's blood without any coagulation promoting substance, but typically after protamine has been administered to the patient. Tube 2B may, for example, have 25 ucg of protamine added. Tube 2C may, for example, have 0.5 cc of fresh frozen plasma, based upon an equivalent dose of 4 units of fresh frozen plasma, added. Tube 2D may, for example, have 0.25 cc of platelets, based upon an equivalent dose of 10 units of platelets, added. Tube 2E may, for example, have 0.1 cc of cryoprecipitate, based upon an equivalent dose of 10 units, added. Tube 2F may, for example, have 2.5 mg of AMICAR, based on an equivalent loading dose of 5 grams, added. Tube 2G may, for example, have 0.002 cc of desmopressin acetate, based upon an equivalent total dose of 0.3 ucg, added. Tube 2H may, for example, have 0.05 cc of aprotinin added. Each tube additionally may have a quantity of diatomaceous earth added or other activator substance.

These equivalent doses are based on a whole blood sample of 2.5 cc. However, the system may be designed to use the smallest volume of whole blood which still offers accurate test results, for example, a sample size ranging from 0.5 to 2.5 cc could easily be used. Further, microliter amounts of a patient's blood may be used without deviating from the scope of the invention. In this case, coagulation may be detected photo-optically, or by, for example, capillary action in a thin tube or up a filter paper. Of course, larger samples may also be used.

The initial time is noted as the test start time when the blood is added to tubes 2A-H, which are then mixed and heated to 37° C. Preferably, this is done for all tubes 2A-H at around the same time. The magnetic detectors or other coagulation detectors then record signal when coagulation occurs or other clotting indicator is detected in a particular tube and the time elapsed for that tube noted.

The wells may additionally contain blood to which has been added a measured amount of citrate ion (typically, as sodium citrate). Citrate ion prevents coagulation function in the blood. Therefore, if there is to be a delay from the time a patient's blood is added to the wells to the beginning of the test, citrate ion therein prevents premature clotting. At the time the test is begun, a measured amount of calcium ion (typically from calcium chloride or calcium gluconate) is added to the blood samples in the well. Calcium ion binds with the citrate ion and thus prevents the citrate ion from inhibiting coagulation, allowing coagulation function to proceed. In operation, samples of the patient's blood are added to the wells and homogeneously mixed with different coagulation promoting substances in each well, reserving at least one well for a blood sample with no coagulation promoting substance to function as a baseline for a control. Then, the test start time is considered to be when the calcium ion is added to each well for binding with the citrate ion. However, the system and method of the invention may be used which includes a different coagulation inhibiting substance. In this case, blood will be prevented from clotting prematurely by using a different coagulation inhibitor, other than citrate ion, which is then counteracted by a different binding or other reversal substance other than calcium ion. In addition, non-ionic inhibitors and coagulation function restorers can be envisioned without departing from the scope of the invention.

In operation, if, for example, after protamine administration, in a patient that is still bleeding, and the HEPCON or other heparin detection system indicates there is no circulating heparin, and there is still bleeding, the inventive system and method would be used and an appropriate coagulation promoting substance to be administered to a patient as a therapy is chosen based on, typically, the first of tubes 2A-H which brought the coagulation time or clotting indicator time closest to the patient's pre-operative baseline control value, typically the pre-operative ACT time. If bleeding continues, the coagulation promoting substance which was the next most effective, i.e., which also brought the coagulation time to a level close to normal times, would be administered. Also, as patients may have bleeding disorders in the face of a normal ACT, the device and method may be used in patients who are bleeding despite normal ACT times, though clotting indicator time detectors other than the ACT may have to be used.

The number of tubes 2 and coagulation promoting substances contained therein may be varied considerably. For example, each tube may contain one of a variety of potential blood clotting agents useful as coagulation promoting substances such as coagulation factors I (fibrinogen), II (prothrombin), IIa (thrombin), III (thromboplastin), IV, V, VI, VII, VIII, IX, X, XI, XII, XIII, recombinant coagulation factors, bovine coagulation factors, coagulation factor VIII:C, Von Willebrand factor, platelets, fibronectin, desmopressin acetate (DDAVP), epsilo-amino caproic acid (AMICAR), cryoprecipitate, fresh frozen plasma, protamine, aprotinin and various mixtures thereof.

Many of the coagulation promoting substances are individual factors implicated in the coagulation cascade. Generally, these factors are collected by partitioning and separating blood products. However, it is recognized that many coagulation factors are now available or will soon be available as the product of recombinant DNA technology. In addition, coagulation factors may obtained from cow or pig serum (bovine and porcine coagulation factors) or are synthesized in a lab (synthetic coagulation factors). The scope of the present invention is not limited to naturally occurring coagulation promoting substances and, in fact recognizes that any substance useful as a therapy for restoring proper coagulation function may be used, whether synthetic or natural.

In addition, individual coagulation factors, both natural and synthetic, and other chemicals can be combined as a single coagulation promoting substance therapy. For example, cryoprecipitate, which is a blood product available from blood banks, contains high concentrations of factor VIII, Fibrinogen (I), von Willebrand factor and fibronectin. See, for example, Hathaway and Goodnight, *Disorders Of Hemostasis And Thrombosis A Clinical Guide*, page 448–449, McGraw Hill, Inc., 1993. As the field of synthetic factors matures, coagulation promoting substances which are a combination of factors may be desirably used. However, care in selecting combinations of factors will need to be considered by the clinician. For example, a combination coagulation promoting substance including factors I, II, von Willebrand factor and fibronectin would initially seem like an excellent treatment for many types of post-operative bleeding. However, this combination may induce a hypercoagulable state. Similarly, any combination of factors in a "shotgun" blood product approach may also induce a hypercoagulable state. The present invention is designed to take into consideration these problems because blood samples which are tested with a combination coagulation promoting substance may show a clotting indicator much sooner than that patient's normal coagulation time (i.e., the elapsed coagulation time of the patient's blood taken prior to the medical procedure and with no coagulation promoting substances added) and the therapy selected accordingly. The system and method of the invention may conveniently be adapted to use specific combinations that the clinician or other user, in their experience, has found potentially useful.

The system and method herein may contain a substantial number or group of wells, or chambers or mixing locations for testing many individual coagulation promoting substances as well as combinations of substances and at varying temperatures. Also, because the test may be completed in a very short time, different sets of coagulation promoting substances may be prepared using a system or method containing a smaller number of wells, but adapted such that the clotting indicator is determined by an automated device. In this case, an initial screening of the patient's blood can be done in one well pack, containing, for example, six wells, one containing the patient's blood without any coagulation promoting substance, and the other five each containing blood product combination coagulation promoting substances, such as fresh frozen plasma, platelets, cryoprecipitate, and/or non-blood product coagulation promoting substances such as DDAVP and AMICAR. Once this test is run, and based on the results, the clinician or other user can select a separate six well pack containing individual coagulation promoting substance factors or chemicals to further narrow the most appropriate treatment. Again, the system and method are easily adaptable to take into account the requirements of a particular clinician or other user. Finally, yet another six well pack containing additive amounts of the coagulation promoting substance to be used as a therapy may be used to help the clinician select an appropriate dose of that coagulation promoting substance.

Preferably, 6–10 tubes 2 are incorporated in the system and and the individual stop times noted and/or recorded automatically, utilizing a suitable instrument control apparatus. Of course, more or less tubes 2 may be used as necessary, as determined in light of experience and most likely or least invasive courses of action. For example, one tube may include both AMICAR and desmopressin acetate since neither carries the risk of disease transmission.

It is also contemplated within the scope of the invention that a tube pack containing 3–5 tubes each, and possibly prefilled with specific coagulation promoting substances as treatment agents would be supplied to the clinician or other user and combined with other packs if needed. Based on experience, severity of hemorrhaging, etc, a clinician or other user could select the appropriate pack(s) for a first run in the system and supplement the choice as needed with different packs.

An automated testing system for determining an appropriate coagulation promoting substance for administration to a patient as a therapy for improving clotting function in said patient is described with reference to FIG. 2. The automated system 10, shown schematically, includes a holder 15 for receiving a patient's blood 35. Holder 15 is in fluid communication with an aliquot meter 55 attached to it for withdrawing measured portions of blood 35 as needed. Blood 35 can be withdrawn from holder 15 by aliquot meter 55, for instance, by aspiration, an electric pump, or a hydro-mechanical pump. Of course, other ways of withdrawing measured samples of blood 35 from holder 15 by aliquot meter 55 can be envisioned without deviating from the scope of this invention such as by pipette, or by a gated channel.

Automated device 10 also contains various reservoirs 95A-D, each of which contains a different individual or combination of coagulation promoting substances 105A-D. For example, reservoir 95A may contain, for example, protamine 105A, reservoir 95B may contain, for example, fresh frozen plasma 105B, reservoir 95C may contain, for example, platelets 105C, and reservoir 95D may contain, for example, cryoprecipitate 105D. Of course, additional reservoirs, containing for example AMICAR, desmopressin acetate, aprotinin, or any of the various other coagulation factors may be envisioned as included in the reservoir set without deviating from the scope of the invention.

Each reservoir 95A-D is in fluid communication with an individual corresponding dosing meter 115A-D. Dosing meters 115A-D are each individually programmed to deliver an appropriate equivalent dose of coagulating promoting substance 105A-D from reservoir 95A-D for representing a predetermined therapy amount appropriate in relation to each metered amount of blood 35. That is, an equivalent amount based on the ratio of some measure of blood volume in the patient to the volume of blood sample used in the wells. Dosing meters 115A-D, like aliquot meter 55 may operate by aspiration, an electric pump, a hydro-mechanical pump, a pipette or a gated channel.

For example, if aliquot meter 55 is programmed to deliver 2.5 cc samples of blood 35, which represents 1/2000th ($5 \times 10^{-4}$) of a 70 kilogram adult with a typical blood volume of 5000 cc, the equivalent doses to be metered by dosing meters 115A-D will be 1/2000th ($5 \times 10^{-4}$) of the amount which would be used as a coagulation function restoring therapy. Thus, using the examples above, dosing meter 115A will be programmed to deliver 25 ucg of protamine, dosing meter 115B will be programmed to deliver 0.5 cc of fresh frozen plasma (based upon a single dose of 4 units of fresh frozen plasma to be delivered to a normal 70 kilogram adult with a blood volume of 5000 cc), dosing meter 115C will be programmed to deliver 0.25 cc of platelets (based upon a dose of 10 units of platelets), and dosing meter 115D will be programmed to deliver 0.1 cc of cryoprecipitate (based upon a dose of 10 units). Of course, if the clinician or other user determines that, for instance, a dose of 2 units of fresh frozen plasma should be tested, then dosing meter 115$b$ in the above example may be conveniently programmed to deliver 0.25 cc of fresh frozen plasma.

In a preferred embodiment, electronic controls will allow for entry of a patient's height and weight and body habitus and conversion information for determining a blood sample size to be delivered from aliquot meter 55 and an equivalent dose size to be delivered from dosing meters 115A-D.

Automated system 10 also contain wells 75A-D corresponding to each reservoir 95A-D and at least one additional well 75E for containing untreated blood 35 as a baseline or a standard which may function as a control. Wells 75A-E each receive a metered sample of blood 35 from holder 15 by being apportioned through aliquot meter 55. Well 75A receives a metered dose of coagulation promoting substance 105A through dosing meter 115A, well 75B receives a metered dose of coagulation promoting substance 105B through dosing meter 115B, and each additional well 75 corresponding to a reservoir 95 receives a metered dose of coagulation promoting substance 105 through dosing meter 115 as appropriate for the number of wells 75, reservoirs 95, and dosing meters 115. At least one additional well 75E contains blood 35 from holder 15 with no coagulation promoting substance 105 added. This additional well 75E is used to determined a baseline or standard coagulation time to function as a control.

Automated system 10 also includes coagulation detectors 125A-E. Coagulation detectors 125A-E may be a photo-optical system or a magnetic system or other systems to evaluate clot formation or other clotting indicator. Additionally, the clot formation evaluating detector may be different for different coagulation promoting substances, i.e., a different clotting indicator may be used to assess the addition of platelets as compared to the clotting indicator for evaluating the addition of plasma. In automated system 10 which includes different coagulation detectors 125A-E, as thus described, it will be typical for a clinician or other user to measure a baseline or normal blood sample clotting time using each of the various clot formation evaluating indicators. Thus, wells 75 corresponding to each of these baseline control samples will be included in automated system 10. In automated system 10 as thus configured, a clinician or other user will evaluate clot formation times or clotting indicator of various blood samples generally as a percentage of the normal baseline clotting time for the sample tested with that particular clot formation evaluating indicator.

The test for determining an appropriate coagulation promoting substance for administration to a patient as a therapy for improving clotting function in said patient begins when the patient's blood 35 is mixed with coagulation promoting substances 105A-D in wells 75A-D. In addition, an additional well 75E contains the patient's blood 35 only. At the start of the test, a timer is started. When coagulation detectors 125A-E detect coagulation or other clotting indicator of blood 35 in well 75A-E coagulation detectors 125A-E send a signal whereby the elapsed time from the start of the test to coagulation in a well 75A-E can be recorded. The clinician evaluates the elapsed times for each well 75A-D containing blood 35 and coagulation promoting substances 105A-D by analyzing the elapsed times it took for coagulation, for example, to occur in that blood 35. Typically, the well 75 in which coagulation occurs first will contain the coagulation promoting substance 105 which should be used as an initial therapy for improving clotting function in that patient.

Wells 75A-E may preferably also be heated to body temperature for maintaining blood 35 in a condition that most closely approximates the patient's circulating blood. Thus, the test is run under conditions that closely simulate the actual conditions for the patient. However, it is often the case that patients who have undergone extensive or lengthy procedures involving extracorporeal circulation or other lengthy surgery, will have a depressed body temperature. It is well-known that depressed body temperatures, or hypothermia, can have a major implication in a patient's coagulation cascade. In fact, compromised coagulation function in a patient may be due to this hypothermia, rather than a lack of any particular coagulation factors, and thus may not be amenable to being restored by a coagulation promoting substance. The mechanisms by which hypothermia may cause compromised coagulation function include thrombocytopenia (low platelet count), decrease in factor levels (particularly fibrinogen, prothrombin, factor VII), increased fibrinolytic, antithrombin and proaccelerin (factor V-like) activity and disseminated intra-vascular coagulation. See, Ratnoff and Forbes *Disorders Of Hemostasis*, Saunders 1991 and Despotis, Filos, et al. *Factors Associated With Excessive Post-Operative Blood Lose and Hemostatic Transfusion Requirements: A Multi-Variant Analysis In Cardiac Surgical Patients*, Anesth. Analg. 82:13–21, 1996.

In order to test whether hypothermia is responsible for a patient's compromised coagulation function, the automated system 10 of the invention may further include temperature controllers 135A-E for each well 75A-E. Thus, wells 75A-E can be maintained at the patient's actual body temperature, or at normal body temperature or some other temperature depending on the choice of the clinician. Ideally, additional wells 75 can be provided which can contain metered aliquots of patient's blood 35 and metered doses of coagulation promoting substance 105 and kept at the patient's actual body temperature by temperature controllers 135, while other, separate wells 75 can contain metered aliquots of blood 35 and metered doses of coagulation promoting substances 105 and kept at normal body temperature. Thus, a clinician evaluating the elapsed time to coagulation in wells 75 maintained at normal body temperature and wells 75 maintained at the patient's actual body temperature can determine which coagulation promoting substance to administer as a therapy for improving clotting function in the patient and whether restoring the hypothermic patient to normal body temperature by itself will be sufficient therapy.

In a preferred embodiment, holder 15 is removable from automated system 10. Thus, holder 15 can receive freshly withdrawn patient's blood 35 which may then be reattached to system 10 for allowing testing of the new blood samples. Holder 15 will additionally contain a measured amount of sodium citrate, which as discussed above, will prevent blood 35 from clotting. In this case, calcium chloride is added to wells 75a–75e to bind with the sodium citrate and allowing clotting to occur. Also, reservoirs 95 may be removable for convenient filling with coagulation promoting substances by a blood bank technician, or the clinician.

Utilizing the inventive system, results are given rapidly, and preferably within about 2 to 5 minutes in an operating or emergency room setting, with the results communicated immediately to the attending personnel. Treatment can be given immediately and selectively targeted to give the most effective results. In many cases, risk of disease transmission is reduced as shotgun therapy of indiscriminately adding various blood products is avoided.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A method for determining at least one appropriate coagulation promoting substance for use in a treatment for arresting bleeding in a patient comprising the steps of:

a) introducing a selected amount of the patient's blood into each of a first group of at least three sample wells;

b) providing a control sample by maintaining at least one of the sample wells free of any coagulation promoting substances;

c) providing test samples by introducing distinct coagulation promoting substances capable of improving clotting function into at least two other sample wells;

d) maintaining each of said sample wells at a first defined temperature;

e) measuring the clotting times of the samples; and f) comparing the clotting time of the control sample to the clotting times of the test samples to determine at least one appropriate coagulation promoting substance to use as a treatment for arresting bleeding in the patient.

2. The method of claim 1, wherein said at least one coagulation promoting substance is selected from the group consisting of coagulation factors, recombinant coagulation factors, bovine coagulation factors, coagulation factor VIII:C, von Willebrand factor, platelets, fibronectin, thrombin, desmopressin acetate, epsilo-amino caproic acid, cryoprecipitate, fresh frozen plasma, protamine, aprotinin and calcium ion.

3. The method of claim 2, wherein the coagulation factors are selected from the group consisting of coagulation factors I, Ia, II, IIa, III, IV, V, VI, VII, VIII, IX, X, XI, XII, and XIII.

4. The method of claim 2, wherein the recombinant coagulation factor is recombinant factor VIII.

5. The method of claim 2, wherein the cryoprecipitate is bovine cryoprecipitate, or human cryoprecipitate.

6. The method of claim 2, wherein the fresh frozen plasma is bovine fresh frozen plasma, or human fresh frozen plasma.

7. The method of claim 1, further comprising the step of mixing said patient's blood in each of said other sample wells with said coagulation promoting substances at substantially the same time.

8. The method of claim 1, wherein said step of measuring clotting times is performed by a plurality of magnetic detectors triggerable by displacement of magnetic rods in each sample well due to blood clotting in any of said sample wells.

9. The method of claim 1, wherein said step of measuring clotting times is performed by a plurality of photo-optical detectors associated with each sample well triggerable by interruption of light transmission from a light source due to blood clotting in any of said sample wells.

10. The method of claim 1 wherein each of said test samples contains substantially equivalent doses of the distinct coagulation promoting substances.

11. The method of claim 1 wherein each of said distinct coagulation promoting substances is tested in different doses for determining the optimal therapeutic dose of the at least one appropriate coagulation promoting substance.

12. The method of claim 1 wherein said first defined temperature is the patient's actual body temperature or the patient's normal body temperature.

13. The method of claim 1, further comprising the steps of:

(g) providing a second group of sample wells with a control sample and at least two test samples as in steps (a) through (c);

(h) maintaining the sample wells of said second group of sample wells at a second defined temperature;

(i) measuring and comparing the clotting times of the samples in said second group of sample wells as in steps (e) and (f); and (j) further comparing the clotting times observed in said second group of sample wells maintained at said second defined temperature with the clotting times observed in said first group of sample wells maintained at said first defined temperature to determine at least one appropriate coagulation promoting substance to use as a treatment for arresting bleeding in the patient.

14. The method of claim 13 wherein said first defined temperature is the patient's actual body temperature and said second defined temperature is the patient's normal body temperature.

15. The method of claim 14, further comprising the steps of:

(k) providing additional groups of sample wells, each with a control sample and at least two test samples as in steps (a) through (c);

(l) maintaining the sample wells of each of said additional groups of sample wells at a defined temperature other than the patient's normal body temperature or the patient's actual body temperature, wherein each additional group of sample wells is maintained at a different defined temperature;

(m) measuring and comparing the clotting times of the samples of each additional group of sample wells as in steps (e) and (f); and (n) further comparing the clotting times observed in each additional group of sample wells with the clotting times observed in said first group of wells maintained at the patient's actual body temperature and with the clotting times observed in said second group of sample wells maintained at the patient's normal body temperature to determine at least one appropriate coagulation promoting substance to use as a treatment for arresting bleeding in the patient.

16. The method of any one of claims 1 through 15, wherein each group contains 4–10 sample wells.

* * * * *